(12) United States Patent
Clineff et al.

(10) Patent No.: US 8,778,378 B2
(45) Date of Patent: Jul. 15, 2014

(54) BIOACTIVE ANTIBACTERIAL BONE GRAFT MATERIALS

(75) Inventors: Theodore D. Clineff, Phoenixville, PA (US); Marissa M. Darmoc, Philadelphia, PA (US); Lauren Brown, Ardmore, PA (US)

(73) Assignee: Orthovita, Inc., Malvern, PA (US)

( * ) Notice: Subject to any disclaimer, the term of this patent is extended or adjusted under 35 U.S.C. 154(b) by 328 days.

(21) Appl. No.: 12/643,002

(22) Filed: Dec. 21, 2009

(65) Prior Publication Data

US 2011/0150963 A1    Jun. 23, 2011

(51) Int. Cl.
| | |
|---|---|
| A61K 9/00 | (2006.01) |
| A61K 33/00 | (2006.01) |
| A61K 33/06 | (2006.01) |
| A61P 31/00 | (2006.01) |

(52) U.S. Cl.
USPC ............................ 424/423; 424/600; 424/682

(58) Field of Classification Search
USPC .................................. 424/426, 423, 600, 682
See application file for complete search history.

(56) References Cited

U.S. PATENT DOCUMENTS

| | | | |
|---|---|---|---|
| 4,851,046 A | 7/1989 | Low et al. | |
| 5,204,106 A | 4/1993 | Schepers et al. | |
| 5,681,872 A | 10/1997 | Erbe | |
| 5,707,962 A | 1/1998 | Chen et al. | |
| 5,834,008 A | 11/1998 | Greenspan et al. | |
| 5,879,717 A | 3/1999 | McConn-Stern et al. | |
| 5,914,356 A | 6/1999 | Erbe | |
| 6,054,122 A | 4/2000 | MacPhee et al. | |
| 6,117,425 A | 9/2000 | MacPhee et al. | |
| 6,123,731 A | 9/2000 | Boyce et al. | |
| 6,190,643 B1 | 2/2001 | Stoor et al. | |
| 6,197,325 B1 | 3/2001 | MacPhee et al. | |
| 6,244,871 B1 | 6/2001 | Litkowski et al. | |
| 6,294,041 B1 | 9/2001 | Boyce et al. | |
| 6,294,187 B1 | 9/2001 | Boyce et al. | |
| 6,383,159 B1 | 5/2002 | Saul et al. | |
| 6,428,800 B2 | 8/2002 | Greenspan et al. | |
| 6,440,444 B2 | 8/2002 | Boyce et al. | |
| 6,478,825 B1 | 11/2002 | Winterbottom et al. | |
| 6,482,427 B2 | 11/2002 | Yang | |

(Continued)

FOREIGN PATENT DOCUMENTS

| | | |
|---|---|---|
| WO | 0076486 A1 | 12/2000 |
| WO | 2006058906 A1 | 6/2006 |
| WO | 2011072212 A2 | 6/2011 |
| WO | 2011127149 A1 | 10/2011 |

OTHER PUBLICATIONS

Allan I, Newman H, Wilson M. Antibacterial activity of particulate Bioglass against supra- and subgingival bacteria. Biomaterials 2001; 22:1683-1687.

(Continued)

*Primary Examiner* — Lezah Roberts
*Assistant Examiner* — Tracy Liu
(74) *Attorney, Agent, or Firm* — Lerner, David, Littenberg, Krumholz & Mentlik, LLP

(57) ABSTRACT

The present invention generally relates to bioactive antibacterial materials and composites that enhance bone growth while preventing surgical site infection. The present invention also relates to bioactive antibacterial materials and composites that include a bimodal bioactive glass particle size distribution. The bioactive antibacterial composite finds utility in a variety of clinical applications including spine and orthopaedic procedures.

16 Claims, 17 Drawing Sheets

(56) References Cited

U.S. PATENT DOCUMENTS

| | | | |
|---|---|---|---|
| 6,482,584 B1 | 11/2002 | Mills et al. |
| 6,521,246 B2 | 2/2003 | Sapieszko et al. |
| 6,559,119 B1 | 5/2003 | Burgess et al. |
| 6,613,278 B1 | 9/2003 | Mills et al. |
| 6,616,698 B2 | 9/2003 | Scarborough |
| 6,652,818 B1 | 11/2003 | Mills et al. |
| 6,696,073 B2 | 2/2004 | Boyce et al. |
| 6,709,744 B1 | 3/2004 | Day et al. |
| 6,756,060 B1 | 6/2004 | Greenspan et al. |
| 6,808,585 B2 | 10/2004 | Boyce et al. |
| 6,843,807 B1 | 1/2005 | Boyce et al. |
| 6,863,694 B1 | 3/2005 | Boyce et al. |
| 6,881,766 B2 | 4/2005 | Hain |
| 6,972,130 B1 | 12/2005 | Lee et al. |
| 6,987,136 B2 | 1/2006 | Erbe et al. |
| 6,991,803 B2 | 1/2006 | Sapieszko et al. |
| 7,001,551 B2 | 2/2006 | Meredith |
| RE39,192 E | 7/2006 | MacPhee et al. |
| RE39,298 E | 9/2006 | MacPhee et al. |
| RE39,321 E | 10/2006 | MacPhee et al. |
| 7,141,073 B2 | 11/2006 | May et al. |
| 7,189,263 B2 | 3/2007 | Erbe et al. |
| 7,189,410 B1 | 3/2007 | Drohan et al. |
| 7,196,054 B1 | 3/2007 | Drohan et al. |
| 7,208,179 B1 | 4/2007 | Drohan et al. |
| 7,229,959 B1 | 6/2007 | Drohan et al. |
| 7,241,459 B2 | 7/2007 | Fechner et al. |
| 7,250,174 B2 | 7/2007 | Lee et al. |
| 7,531,004 B2 | 5/2009 | Bagga et al. |
| 7,534,451 B2 | 5/2009 | Erbe et al. |
| 7,595,043 B2 | 9/2009 | Hedrick et al. |
| 7,608,258 B2 | 10/2009 | Mishra |
| 7,615,030 B2 | 11/2009 | Murphy et al. |
| 7,691,839 B2 | 4/2010 | Glidden |
| 7,722,678 B2 | 5/2010 | Brown et al. |
| 7,749,555 B2 | 7/2010 | Zanella et al. |
| 7,771,716 B2 | 8/2010 | Hedrick et al. |
| 7,838,022 B2 | 11/2010 | Drapeau et al. |
| 7,939,092 B2 | 5/2011 | McKay et al. |
| 7,955,616 B2 | 6/2011 | Kronenthal |
| 8,012,501 B2 | 9/2011 | Kerr et al. |
| 8,039,016 B2 | 10/2011 | Drapeau et al. |
| 8,057,595 B2 | 11/2011 | Armitage et al. |
| 8,066,695 B2 | 11/2011 | Muto et al. |
| 2005/0288795 A1 | 12/2005 | Bagga et al. |
| 2007/0218098 A1 | 9/2007 | Reif et al. |
| 2008/0187571 A1 | 8/2008 | Clineff et al. |
| 2008/0221701 A1* | 9/2008 | Zhong et al. ............ 623/23.62 |
| 2009/0324683 A1 | 12/2009 | Evans et al. |

OTHER PUBLICATIONS

Alan I, Newman H, Wilson M. Particulate Bioglass reduces the viability of bacterial biofilms formed on its surface in an vitro model. Clin Oral Impl Res 2002, 13-53-58.

Gubler M, Brunner TJ, Zehnder M, et al. Do bioactive glasses convey a disinfecting mechanism beyond a mere increase in pH? International Endodontic Journal 2008; 41:670-678.

Hu S Chang J, Liu M, Ning C. Study on antibacterial effect of 45S5 Bioglass. J Mater Sci: Mater Med 2009; 20:281-286.

Munukka E., Lepparanta 0, Korkeamaki M, et al. Bactericidal effects of bioactive glasses on clinically important aerobic bacteria. J Mater Sci: Mater Med 2008; 19(1):27-32.

Oonishi H, Kushitani S, Yasukawa E, et al. Particulate Bioglass compared with hydroxyapatite as a bone graft substitute. Clin Orth and Rel Res 1997; (334):316-325.

Stoor P, Soderling E, Salonen JI. Antibacterial effects of a bioactive glass paste on oral microorganisms. Acta Odontol Scand 1998; 56(3):161-165.

Wilson J, Pigott GH, Schoen FJ, Hench L1. Toxicology and biocompatibility of bioglasses. J Biomed Mater Res 1981; 15:805-817.

Havener MB, Brown LS, Darmoc MM, et al. Improvements in healing with a bioactive bone graft substitute in a canine metaphyseal defect. Presented at the 55th Annual Meeting of the Orthopedic Research Society, Las Vegas, NV. (2009).

Brown LS, Darmoc MM, Havener MB, et al. Antibacterial effects of 45S5 bioactive glass against four clinically relevant bacterial species. Presented at the 55'" Annual Meeting of the Orthopedic Research Society, Las Vegas, NV. (2009).

Hench et al Bonding mechanism at the interface of ceramic prosthetic materials. J. Biomed. Mater. Res. 5:117-141 (1971).

Kokubo and Takadama, How useful is SBF in predicting in vivo bone bioactivity?. Biomaterials (2006) 27: 2907-2915.

Piotrowski et al., Mechanical studies of the bone bioglass interfacial bond. J. Biomed. Mater. Res. (1975) 9:47-61.

Stanley et al., Residual alveolar ridge maintenance with a new endosseous plant material. Journal of Prostetic Dentistry, vol. 58, pp. 607-613 (1987).

Kingery, W.D. et al (Eds), Introduction to Ceramics, 2nd Ed., John Wiley & Sons 1960, 416.

Robson, Wound Infection: a failure of wound healing caused by an imbalance of bacteria. (1997) Surg Clin North Am. pp. 637-650.

Arumugam et al., Journal of Biomedical Materials Research, 80, Part A, pp. 391-298, 2007.

Balagna et al., J. Biomater. Appl., vol. 00, pp. 1-22, Mar. 5, 2010.

Balamurugan et al., Dental Materials, 24, pp. 1343-1351, 2008.

Bellantone et al., Antimicrobial Agents and Chemotherapy, vol. 46, No. 6, pp. 1940-1945, Jun. 2002.

Bosetti et al., Biomaterials, 23, pp. 887-892, 2002.

Bosetti et al., Biomaterials, 26, pp. 3873-3879, 2005.

Burrell, Ostomy Wound Management, vol. 49, Issue 5A, Suppplement, pp. 19-24, 2003.

Catauro et al., Journal of Materials Science: Materials in Medicine, 15, pp. 831-837, 2004.

Diaz et al., Journal of Nanomaterials, Research Article ID 498505, vol. 2009, 6 pages, 2009.

Farrah et al., Can J. Microbiol, vol. 37, pp. 445-449, 1991.

Feng et al., J of Biomed Mater Res, 52, pp. 662-668, 2000.

Furr et al., Journal of Hospital Infection, 27, pp. 201-208, 1994.

Jones et al. J Mater Sci: Mater Med, 17, pp. 989-996, 2006.

Kawashita et al., Biomaterials, 21, pp. 393-398, 2000.

Kawashita et al., J Biomed Mater Res 66A: pp. 266-274, 2003.

Kramer et al., Clinical Orthopaedics and Related Research, No. 161, pp. 154-162, Nov. 12, 1981.

Lansdown, EE, Clinical, A Review of the Use of Silver in Wound Care, Facts and Fallacies, Jan. 2004.

Liau et al., Letters in Applied Microbiology, 25, pp. 279-283, 1997.

Liu et al., J Biomed Mater Res Part A: 94A, pp. 499-508, 2010.

Luo et al., J Biomed Mater Res Part B: Appl Biomater, 95B, pp. 441-448, 2010.

Matsumoto et al., Acta Biomaterialia, 5, pp. 3157-3164, 2009.

Nand et al., J Indian Med Assoc, vol. 94, No. 3, pp. 91-95, Mar. 1996.

Newby et al., J Mater Med, 22, pp. 557-569, 2011.

Outpatient Surgery, The Arthrex Power Equation, Outpatient Surgery Weekly Newsletter Mar. 8, 2011.

Rameshbabu et al., J Biomed Mater Res, 80A, pp. 581-591, 2007.

Raucci et al., J Biomed Mater Res, Part B, Appl Biomater, 92B, pp. 102-110, 2010.

Sankar et al., J Roy Soc Health, vol. 118, No. 6, pp. 371-374, 1998.

Seeley et al., J Biomed Mater Res 82A: 113-121, 2007.

Shimazaki et al., J Biomed Mater Res, Part B, Appl Biomater, 92B, pp. 386-389, 2010.

Shirkhanzadeh et al., Journal of Materials Science, Materials in Medicine, 9, pp. 385-391, 1998.

Ohta et al., Biol. Pharm. Bull. 1, 42-47, 1999.

Jones et al., "Dose-Dependent Behavior of Bioactive Glass Dissolution", Centre for Tissue Regeneration, Department of Materials, Imperial College of Science, Technology and Medicine, London, United Kingdom, 2001, pp. 720-726.

Sepulveda et al., "In vitro dissolution of melt-derived 45S5 and sol-gel derived 58S bioactive glasses", Department of Materials, Centre of Tissue Regineration and Repair, Imperial College of Sci-

(56) References Cited

OTHER PUBLICATIONS ence, Technology and Medicine, London, United Kingdom, 2001, pp. 301-311.
Waltimo et al., "Antimicrobial Effect of Nanometric Bioactive Glass 45S5", Research Reports Biomaterials & Bioengineering, J Dent Res 86(8): pp. 754-757, 2007.
Wilson et al., "Bioactive Ceramics for Periodontal Treatment: Comparative Studies in the Patus Monkey", Journal of Applied Biomaterials, vol. 3, 123-129 (1992).
Inernational Search Report and Written Opinion for Application No. PCT/US2013/022712 dated Apr. 3, 2013.

* cited by examiner

SEM showing the bimodal size range of glass
(top x50, middle x250, bottom x500).

Depicts a scanning electron microscope (SEM) photograph of the present invention comprising beta-tricalcium phosphate and collagen and Combeite glass-ceramic (< 53 μm and 90 μm – 150 μm).

Particle size distribution of bimodal glass according to the present invention.

Depicts an SEM photograph of the embodiment shown in FIG. 10 after immersion in SBF for 1 day.

Depicts an SEM photograph of the embodiment shown in FIG. 10 after immersion in SBF for 3 days.

Depicts an SEM photograph of the embodiment shown in FIG. 10 after immersion in SBF for 7 days.

Depicts an SEM photograph of the embodiment shown in FIG. 10 after immersion in SBF for 14 days.

Faxitron image of the present invention in pliable pack form at 100 and 200mg/mL (after being wetted) in comparison to control materials.

Viability of bacteria as a function of glass concentration incorporated into a bone graft substitute of collagen and calcium phosphate.

ial graft material in cylinder form. FIG. 2B depicts the graft
BIOACTIVE ANTIBACTERIAL BONE GRAFT MATERIALS

TECHNICAL FIELD

The present invention relates to bioactive antibacterial materials. More particularly, the present invention relates to bioactive antibacterial bone graft compositions including bioactive glass particles having a bimodal size range. The present invention also relates to various methods of treatment in the field of spine and orthopaedics including the use of such bioactive antibacterial bone graft materials and compositions.

BACKGROUND OF THE INVENTION

Surgical site infections (SSI) present a significant clinical problem in both spine and orthopaedic surgery. As well as being costly to the health care system, these infections interfere with wound healing and therefore prolong recovery time for patients. There is a need in the field for treatments to prevent surgical site infections at the local delivery site. The present invention addresses this need by providing a composite biomaterial that includes an antibacterial component for preventing surgical site infections.

Biomaterials, including various metals, polymers and ceramics, have been used as implant materials in the field of spine, orthopaedics and dentistry including fusion, trauma, fracture repair, reconstructive surgery and alveolar ridge reconstruction, for over a century due to their biocompatibility and physical properties. Among these biomaterials, porous calcium phosphate-based bone grafts are known in the art for use in filling bony voids or gaps in the skeletal system. Examples of such bone grafts are described in, for example, U.S. Pat. No. 6,991,803; U.S. Pat. No. 6,521,246; and U.S. Pat. No. 6,383,519; No. incorporated herein. Vitoss® Bone Graft Substitute (Orthovita, Inc., Malvern Pa.) is one exemplary type of such bone grafts. Such porous calcium phosphate-based bone grafts have been further modified and improved to incorporate biocompatible materials such as, for example, polymers including collagen, to impart improved handling ability of the bone graft; and bioactive glasses, to further enhance the biological activity of the bone graft. Examples of such materials are described in, for example, U.S. Pat. No. 7,534,451; U.S. Pat. No. 7,531,004; U.S. Pat. No. 7,189,263 and U.S. Patent App. No. 20080187571, incorporated herein. Vitoss™ BA Bioactive Bone Graft Substitute (Orthovita, Inc., Malvern, Pa.) is one exemplary type of such a bone graft incorporating bioactive glass.

Bioactive (BA) glasses have been extensively studied for their bone bonding properties. The use of BA glass alone and in combination with other materials is generally described in U.S. Pat. No. 5,681,872; U.S. Pat. No. 5,914,356; and U.S. Pat. No. 6,987,136, each of which is assigned to the assignee of the present invention and is incorporated in this document by reference in its entirety.

The wound healing and bactericidal properties of BA glasses have also been reported, particularly BA glasses of certain particle size ranges. U.S. Pat. No. 6,756,060; U.S. Pat. No. 6,428,800 and U.S. Pat. No. 5,834,008 describe wound and burn dressings comprising BA glass. However, the BA glass is generally combined with topical antibiotic and incorporated into bandages.

Accordingly, there is a need in the art for implant materials and composites that induce bone formation and prevent surgical site infections. There is also a need in the art for a method of preparing a homogeneous bioactive antibacterial composite; and for methods of using bioactive antibacterial materials and composites in a variety of clinical applications including spine and orthopaedic procedures. The present invention fulfills these needs. It has been discovered that materials that include bioactive glass in a specific bimodal glass size distribution alone and incorporated within a collagen matrix along with calcium phosphate produce a bioactive antibacterial implant that successfully enhances bone growth and inhibits surgical site infection.

BRIEF DESCRIPTION OF SEVERAL VIEWS OF THE DRAWINGS

The invention is best understood from the following detailed description when read in connection with the accompanying figures. It is emphasized that, according to common practice, the various features of the figures are not to scale. On the contrary, the dimensions of the various features are arbitrarily expanded or reduced for clarity. Included are the following figures:

FIG. 9A—×50 magnification (top), FIG. 9B—×250 magnification (middle), FIG. 9C—×500 magnification (bottom).

DETAILED DESCRIPTION OF THE INVENTION

Figure 1:
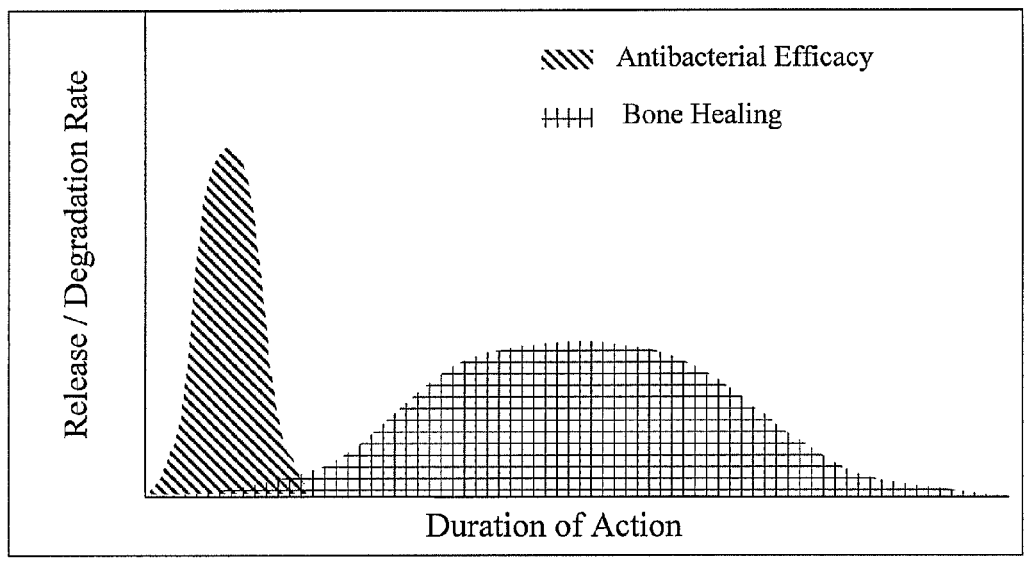
FIG. 1 is a graphical depiction of the in-vivo release and degradation profile of the bioactive antibacterial material of the present invention.

The present invention generally relates to bioactive antibacterial implant materials capable of preventing surgical site infection, and, more particularly to bioactive antibacterial materials that include bioactive glass in a specific bimodal glass size distribution. The present invention also relates to flexible and pliable bioactive antibacterial composites of biocompatible polymer, ceramic and bioactive glass having a bimodal glass size distribution. The present invention further relates to methods of repairing or fusing bone; and methods of facilitating bone repair while preventing surgical site infection.

The present invention provides bioactive antibacterial materials and composites comprising bioactive and biocompatible implant materials for formulation of shaped bodies capable of inducing bone formation and preventing surgical site infection. The present invention also provides bioactive composites that can be locally delivered and have the appropriate properties to prevent surgical site infection while stimulating bone formation. The present invention also provides for shaped bodies prepared from these materials and compositions to be used in a wide array of clinical applications including spinal and orthopaedic procedures.

As used herein, the term "antibacterial" refers to a material that is capable of killing bacteria outright or a material that is able to stop additional growth of bacteria.

In one embodiment, the present invention provides bioactive antibacterial materials that include bioactive glass having particles with a particle size of less than about 53 microns (μm) and particles of a particle size range from about 90 microns (μm) to about 150 microns (μm).

In another embodiment, the present invention provides bioactive antibacterial composites that include a biocompatible polymer and an inorganic ceramic in combination with bioactive glass having a bimodal glass size distribution. As used herein, the term "biocompatible polymer" refers to a polymer that, when introduced into a living system, will be compatible with living tissue or the living system (e.g., by not being substantially toxic, injurious, or not causing immunological rejection). In the present invention, the biocompatible polymer may be selected such that it will function to reinforce the composite in order to, for example, provide flexibility, pliability and structure to the composite.

Bioactive glasses and bioactive glass-ceramics are characterized by their ability to form a direct bond with bone. In small particle size ranges (<90 μm), these materials have also been reported to be antibacterial, however, are not optimal for inducing bone formation. Until now, the synergistic nature of a bioactive glass material that has both optimal antibacterial properties and is capable of inducing bone formation (termed "dual action" throughout this document) has not been explored. Furthermore, a porous composite implant that is flexible and pliable and includes a synergistic bioactive glass of this type, heretofore, has not been developed.

An implant that includes antibacterial, bone-bonding and bone inducing properties is desirable. By incorporating bioactive glass into a porous substrate comprised of beta-tricalcium phosphate and collagen in a specified bimodal particle size range, a porous composite material is formed that is pliable and which has antibacterial properties and bioactive properties that lead to appropriate bone formation (e.g., bone formation concurrent with implant resorption). It has been particularly determined that a composite material having bioactive glass in a bimodal particle size range distribution that includes both 1) about less than or equal to 53 μm glass particles and 2) from about 90 μm to about 150 μm glass particles facilitates bone growth and prevents surgical site invention.

The bioactive glass used in the present invention may be any alkali-containing ceramic (glass, glass-ceramic, or crystalline) material that reacts as it comes in contact with physiological fluids including, but not limited to, blood and serum, which leads to bone formation. In preferred embodiments, the bioactive glasses, when placed in physiologic fluids, form an apatite layer on their surface. As used herein, "bioactive" relates to the chemical formation of a calcium phosphate layer (amorphous, partially crystalline, or crystalline) via ion exchange between surrounding fluid and the composite material. Bioactive also describes materials that, when subjected to intracorporeal implantation, elicit a reaction. Such a reaction leads to bone formation, attachment into or adjacent to the implant, and/or bone formation or apposition directly to the implant, usually without intervening fibrous tissue.

Preferably, the bioactive glass component of the present invention comprises regions of Combeite crystallite morphology. Such bioactive glass is referred to in this document as "Combeite glass-ceramic". Examples of preferred bioactive glasses suitable for use in the present invention are described in U.S. Pat. No. 5,681,872 and U.S. Pat. No. 5,914,356, each of which is incorporated by reference in this document in its entirety. Other suitable bioactive materials include 45S5 glass and compositions comprising calcium-phosphorous-sodium silicate and calcium-phosphorous silicate. Further bioactive glass compositions that may be suitable for use in the present invention are described in U.S. Pat. No. 6,709,744, incorporated in this document by reference. Additionally, bioactive materials such as borosilicate, silica, borate, phosphate-containing materials and Wollastonite may also be used. It is understood that some non-alkali-containing bioactive glass materials are within the spirit of the invention. For example, non-alkali containing glass may be substituted for one or both of the bimodal particle size ranges. In certain embodiments, the larger particle size material (90 μm-150 μm) may be, for instance, borosilicate, silica, or Wollastonite bioactive glass. In some embodiments, the smaller particle size material (<53 μm) material may contain silver, or another potent antibacterial agent, as part of its composition rather than an alkali agent. It should be understood that multiple combinations of alkali and non-alkali containing materials are possible, while maintaining the dual action of antibacterial properties and bone healing properties afforded by a bimodal particle size distribution. Bioactive glasses, as defined in this document, do not include calcium phosphate materials, for example, hydroxyapatite and tricalcium phosphate. However, in addition to bioactive glass, the bioactive antibacterial composition of the present invention may additionally include other materials such as calcium phosphate materials.

In preferred embodiments of the present invention, the bioactive glass is Combeite glass-ceramic (also referred to as "Combeite"). Combeite is a mineral having the chemical composition $Na_4Ca_3Si_6O_{16}(OH)_2$. It has been found that the use of bioactive glass in restorative compositions, which bioactive glasses include Combeite crystallites in a glass-ceramic structure (hence, Combeite glass-ceramic), in accordance with the present invention gives rise to superior spinal, orthopaedic and dental restorations.

It is preferred that the Combeite glass-ceramic particles which form some or all of the bioactive glass component of the present invention comprise at least about 2% by volume of Combeite crystallites. Combeite glass-ceramic particles containing higher percentages of crystallites are more preferred and volume percentage from about 5% to about 50% of crystallites are particularly desired. It will be appreciated that the Combeite glass-ceramic particles of the present invention are heterogeneous in that they comprise a glassy, amorphous structure having crystallites or regions of Combeite crystallinity dispersed throughout the material.

In one embodiment of the present invention, the heterogeneous particles of Combeite glass-ceramic have average particle sizes of from less than about 150 μm, while still maintaining at least two distinct particle size distributions. In other embodiments of the present invention, two particular Combeite glass-ceramic average particle size ranges have been found to be preferred, in combination, when practiced with the present invention. The first range is less than or equal to about 53 μm. The second average particle size range is from about 90 μm to about 150 μm. The combination of these two ranges practiced together with the present invention is referred to throughout this application as the bimodal particle size range and/or bimodal particle size distribution.

Methods of determining particle sizes are known in the art. Some methods include passing the particles through several sieves to determine general particle size ranges. Other methods include laser light scattering, and still others are known to persons skilled in the art. Determination of particle size is conveniently accomplished by sieving and such may be used here. Particle size may also be determined via SEM image analysis. It will be appreciated that recitation of averages or size ranges is not meant to exclude every particle with a slightly higher or lower dimension. Rather, sizes of particles are defined practically and in the context of this invention.

In accordance with some preferred embodiments, blends of Combeite glass-ceramics may be useful as the bioactive glass component of the present invention. Thus, a number of different Combeite glass-ceramics can be prepared having different properties, such as Combeite crystallite size, percentage of Combeite crystallites, and the like. It is also preferred in some cases to admix Combeite glass-ceramic in accordance with the present invention with other agents which are consistent with the objectives to be obtained. Thus, a wide variety of such other materials may be so employed so long as composition of the invention comprises bioactive glass equaling at least about 5% by weight of the composition.

In certain embodiments, the bioactive glass component may be in the form of fibers, whiskers or strands. It is preferred that the diameters of these fibers and strands also be bimodal with a first average diameter size of less than or equal to about 53 μm and a second average diameter size range from about 90 μm to about 150 μm.

In some embodiments, the bioactive glass comprises at least one alkali metal such as, for example, lithium, sodium, potassium, rubidium, cesium, francium, or combinations of these metals. In other embodiments, however, the bioactive glass has little to no alkali metal. For example, in certain embodiments, the bioactive glass has 30% or less of alkali metal. In other embodiments, the bioactive glass has 25% or less of alkali metal. In yet other embodiments, the bioactive glass has 20% or less of alkali metal. In yet other embodiments, the bioactive glass has 15% or less of alkali metal. In other embodiments, the bioactive glass has 10% or less of alkali metal. In still other embodiments, the bioactive glass has 5% or less of alkali metal. In yet other embodiments, the bioactive glass has substantially no alkali metal. However, in these embodiments another antibacterial agent such as silver may be substituted for the alkali metal.

In exemplary embodiments of the present invention, the bioactive glass also has osteoproductive properties. As used in this document, "osteoproductive" refers to an ability to allow osteoblasts to proliferate, allowing bone to regenerate. "Osteoproductive" may also be defined as conducive to a process in which a bioactive surface is colonized by osteogenic stem cells and which results in more rapid filling of defects than that produced by merely osteoconductive materials. Combeite glass-ceramic is an example of an osteoproductive, bioactive material.

According to one embodiment of the present invention, the composite material may comprise up to about 80% of the bioactive glass with about 50% by weight of this glass having a particle size range of less than or equal to about 53 μm and about 50% by weight having a second average diameter size range from about 90 μm to about 150 μm. In certain embodiments, the bimodal bioactive glass is present in an amount of about 10 to 50% by weight of the composite material.

In other embodiments, the present invention material is comprised entirely of bioactive glass (e.g. 100% by weight).

The relative percentage of small (<53 μm) and large bioactive glass particles (90 μm-150 μm) within the present invention may be tailored based on the desired antibacterial efficacy and bone formation. In preferred embodiments of the present invention, about 50% by weight of the bioactive glass particles are from the smaller distribution and about 50% by weight of the bioactive glass particles are from the larger distribution. In embodiments in which the antibacterial efficacy is increased by the addition of another material such as silver, the percentage of small bioactive glass particles may be less than about 25% by weight of the total amount of bioactive glass and the large bioactive glass particles may be about 75% or more by weight of the total amount of bioactive glass. In yet other embodiments, the percentage of small particles may be about 75% or more by weight of the total amount of bioactive glass while the percentage of large particles may be about 25% or less by weight of the total amount of bioactive glass. For instance, the present invention may be tailored to provide greater antibacterial efficacy in compromised sites by increasing the percentage of small particle size glass and correspondingly decreasing the amount of large particle size glass.

The benefits of the present invention reside in the dual action afforded by the bimodal particle size range. While not being bound by a specific mechanism of action, it is believed that the high surface area of the small particles (<53 µm), results in an early burst release of ions and a quick resorption (e.g., 4 weeks or less) that is ideal for the materials and composites of the present invention. Specifically, the antibacterial effect of the small particles commences immediately and continues several weeks until the bacteria are effectively killed off. At this time, the small particles completely resorb, are absent from the site of healing and make way for cells and vessels that aid in bone healing. The large particles (90 µm-150 µm) with lower surface area, more slowly release the ions that create an environment which stimulates osteoblasts for the formation of bone. The bone grows over time as the larger glass particles resorb, however, the large particles are able to provide a substrate for the bone growth prior to resorbing (e.g., 24-52 weeks).

FIG. 1 is a graphical depiction of the in-vivo ion release and degradation profile of the bioactive antibacterial material of the present invention. The profile demonstrates the bimodal particle size distribution with the smaller particle sizes (<53 µm) displaying faster resorption kinetics than the larger particle size (90 µm-150 µm). As described above, the increased surface area of the small particles leads to burst release of ions. In contrast, the larger particles have a slower dissolution rate and therefore require a longer period of time for complete resorption. This larger particle size range also lends itself to partial dissolution and partial cell-mediated resorption.

In certain embodiments, the present invention comprises calcium phosphate having macroporosity, mesoporosity, and microporosity. More preferably, the porosity of the calcium phosphate is interconnected and highly porous. The preparation of preferred forms of calcium phosphate for use in the present invention is described in U.S. Pat. No. 6,383,519 and U.S. Pat. No. 6,521,246, incorporated into this application by reference in their entireties. An exemplary calcium phosphate product is Vitoss® Bone Graft Substitute (available from Orthovita, Inc. of Malvern, Pa.).

The present invention composite may be formed into a variety of shapes or may be cut or shaped at the time of surgery. In other embodiments, the bioactive composite implant is used to fill cavities of metal or non-resorbable implants. For instance, when used with a shaped spinal implant, the present invention composite material may be present within the center cavity of the implant to facilitate fusion of the adjacent vertebral bodies.

In a preferred embodiment of the present invention, a bioactive antibacterial composite is formed upon combining a resorbable biocompatible polymer with resorbable calcium phosphate and resorbable bioactive glass as described in the present invention.

The biocompatible polymer used in the present invention is preferably a natural polymer. Examples of natural biocompatible polymers that are suitable for use in the present invention alone or in combination include collagen and similar organic biomaterials and natural biocompatible polymers. Suitable collagens are described, for example, in U.S. Pat. No. 7,189,263, which is herein incorporated by reference in its entirety. Some embodiments of the present invention contain collagen that comprises up to 100% Type I collagen. In other embodiments, the collagens used may be predominantly, or up to about 90%, of Type I collagen with up to about 5% of Type III collagen or up to about 5% of other types of collagen. Suitable Type I collagens include native fibrous insoluble human, bovine, porcine, or synthetic collagen, soluble collagen, reconstituted collagen, or combinations thereof.

In a preferred embodiment of the present invention, the biocompatible polymer is Type I bovine collagen; and the calcium phosphate is tricalcium phosphate and, more preferably beta-tricalcium phosphate, with a total porosity of at least about 30% and a particle size range of from about 0.25 mm to about 2 mm. Porous calcium phosphate morsels to be used with the present invention are preferably greater than about 0.25 mm in size. The morsels of calcium phosphate may be about 1-2 mm in size for some embodiments of the present invention. The calcium phosphate morsels may be about 0.25 mm to about 1 mm or to about 2 mm for other embodiments of the present invention. For flowable compositions of the present invention, it will be appreciated that the morsel size will be selected considering the desired delivery apparatus. For example, for delivery of a flowable composition using a standard syringe, it will be necessary to select a morsel size that fits through the syringe orifice. Selection of the appropriate morsel size is believed to be with the capability of the skilled artisan.

In preferred embodiments of the present invention, the bioactive glass component has a bimodal glass particle size range with a first glass particle size from about less than or equal to 53 µm and a second glass particle size range from about 90 µm to about 150 µm.

In some embodiments, the bioactive antibacterial composite of the present invention will comprise about 10-80% by weight of calcium phosphate; about 5-20% by weight of collagen; and about 5-80% by weight of bimodal bioactive glass. In other embodiments, the bone graft materials of the present invention will comprise about 50-90% by weight of calcium phosphate; about 5-25% by weight of collagen, and about 5-40% by weight of bioactive glass. In certain embodiments, bone graft materials of the present invention comprise calcium phosphate, collagen, and bimodal bioactive glass in a weight ratio of about 70:20:10. In other embodiments, the weight ratio of calcium phosphate, collagen, and bioactive glass is about 80:10:10. In yet others, the weight ratio of calcium phosphate, collagen, and bioactive glass is about 80:15:5. In further embodiments, the weight ratio of calcium phosphate, collagen, and bimodal bioactive glass is about 50-55 calcium phosphate:10-15 collagen:30-40 bimodal bioactive glass. In others, the weight ratio of calcium phosphate, collagen, and bioactive glass is about 10:10:80. The weight ratio of the calcium phosphate, collagen, and bioactive glass may also be about 60:20:20. In a preferred embodiment, the weight ratio of the calcium phosphate, collagen, and bioactive glass is about 65:15:20. The mass ratios may be altered without unreasonable testing using methods readily available in the art while still maintaining all the properties that attribute to an effective bone graft. One unique feature of the bone graft materials of the present invention is that the mineral remains porous even when combined with the collagen and bioactive glass. Further, the resultant composite bone graft is itself highly porous with a broad pore size distribution as described herein.

The use of collagen has been determined to provide flexible, pliable, or flowable handling properties to the composite so that in addition to being antibacterial, osteoproductive and bioactive, the composite bone graft can also be manipulated, for example, wrapped, cut, bended, and/or shaped, particularly when wetted to fill defects of various sizes. In addition, the porosity of the calcium phosphate imparts porosity to the composite that enables bone growth to occur concurrent with implant resorption by promoting capillary action of fluids, allowing recruitment of cells for bone formation, and permitting angiogenesis.

In preferred embodiments, the composite material comprises varying levels of pore sizes that are interconnected. In exemplary embodiments of the invention, the bone grafts comprise three different porosity size ranges, herein described as macroporosity, mesoporosity, and microporosity. Preferably, the macroporosity, mesoporosity, and microporosity occurs simultaneously. Within the scope of this invention, macroporosity is defined as having pore diameters greater than or equal to 100 microns. Mesoporosity is defined as having a pore diameter less than 100 microns but greater than or equal to 10 microns. Microporosity is defined as having a pore diameter less than 10 microns.

Persons skilled in the art can easily determine whether a material has each type of porosity through examination, such as through the preferred method of scanning electron microscopy. While it is certainly true that more than one or a few pores within the requisite size range are needed in order to characterize a sample as having a substantial degree of that particular form of porosity, no specific number of percentage is called for. Rather, a qualitative evaluation by persons skilled in the art shall be used to determine macroporosity, mesoporosity, and microporosity.

While the invention does not require a specific percentage for each of the three porosity size ranges described, certain percentages of each porosity size range have been found to be particularly well suited for bone graft materials of the present invention. For example, in certain embodiments, the bone graft materials can be characterized as having about 10-25% of the pores within the microporosity range; about 50-70% of the pores within the mesoporosity range; and about 10-30% of the pores within the macroporosity range.

It will be appreciated that in some embodiments, the overall porosity of materials prepared in accordance with this invention is high. This characteristic is measured by pore volume, expressed as a percentage. Zero percent pore volume refers to a fully dense material, which, perforce, has no pores at all. One hundred percent pore volume cannot meaningfully exist since the same would refer to "all pores" or air. Persons skilled in the art understand the concept of pore volume, however and can easily calculate and apply it. For example, pore volume may be determined in accordance with Kingery, W. D., Introduction to Ceramics, Wiley Series on the Science and Technology of Materials, $1^{st}$ Ed., Hollowman, J. H., et al. (Eds.), Wiley & Sons, 1960, p. 409-417, who provides a formula for determination of porosity. Expressing porosity as a percentage yields pore volume. The formula is: Pore Volume=$(1-f_p)$ 100%, where $f_p$ is fraction of theoretical density achieved.

Porosity can be measured by methods known in the art such as helium pycnometry. This procedure determines the density and true volume of a sample by measuring the pressure change of helium in a calibrated volume. A sample of known weight and dimensions is placed in the pycnometer, which determines density and volume. From the sample's mass, the pycnometer determines true density and volume. From measured dimensions, apparent density and volume can be determined. Porosity of the sample is then calculated using (apparent volume−measured volume)/apparent volume. Porosity and pore size distribution may also be measured by mercury intrusion porosimetry, another method known in the art.

Pore volumes in excess of about 30% may be achieved in accordance with this invention while materials having pore volumes in excess of 50% or 60% may also be routinely attainable. Some embodiments of the invention may have pore volumes of at least about 70%. Other embodiments have pore volumes in excess of about 75% or about 80%. Pore volumes greater than about 85% are possible, as are volumes of about 90%. In preferred cases, such high pore volumes are attained while also attaining the presence of interconnected macro-meso-, and microporosity as well as physical stability of the materials produced. It is believed to be a great advantage to prepare graft materials having macro-, meso-, and microporosity simultaneously with high pore volumes that also retain some compression resistance and flexibility, moldability, or flowability when wetted.

Due to the high porosity and broad pore size distribution of the present invention composite graft, the implant is not only able to wick/soak/imbibe materials very quickly, but is also capable of retaining them. A variety of fluids could be used with the present invention including blood, bone marrow aspirate, saline, antibiotics and proteins such as bone morphogenetic proteins (BMPs). Materials of the present invention can also be imbibed with cells (e.g., fibroblasts, mesenchymal, stromal, marrow and stem cells), platelet rich plasma, other biological fluids, and any combination of the above. Bone grafts of the present invention actually hold, maintain, and/or retain fluids once they are imbibed, allowing for contained, localized delivery of imbibed fluids and rapid release of ions from the bioactive glass. In this manner, fluids activate the present invention bioactive glass material. This capability has utility in cell-seeding, drug delivery, and delivery of biologic molecules as well as in the application of bone tissue engineering, orthopaedics, and carriers of pharmaceuticals.

Bioactive antibacterial composites and shaped bodies of the present invention made from the composites preferably demonstrate properties suitable for use in spinal and orthopaedic procedures. Bioactive antibacterial composites and shaped bodies of the present invention made from the composites also preferably demonstrate bioactivity. A formed bioactive composite material according to the present invention can be placed in or near bone voids to facilitate new bone growth while preventing surgical site infection. After some time in the body, the implanted material will begin to bridge the void or facilitate fusion of adjacent bony structures thereby restoring and repairing the site.

It will be appreciated by those skilled in the art that the bioactive antibacterial composites of the present invention may be used in a wide variety of restorative and surgical procedures. One example is the repair or fusion of vertebrae of the spine. Lower back pain may oftentimes be attributed to the rupture or degeneration of lumbar intervertebral discs due to degenerative disc disease, ischemic spondylolisthesis, post laminectomy syndrome, deformative disorders, trauma, tumors and the like. This pain may result from the compression of spinal nerve roots by damaged discs between the vertebra, the collapse of the disc, and the resulting adverse effects of bearing the majority of the patient's body weight through a damaged unstable vertebral joint. To remedy this, spinal implants may be inserted between the vertebral bodies to stabilize and support the joint and facilitate fusion via bone bonding. To facilitate the fusion, bone graft substitute materials such as the material of the present invention are placed in or around the spinal implant to facilitate bone ingrowth prior to resorbing. It is envisioned that the present invention composite material would serve well as a bone graft substitute.

In other embodiments of the present invention, the composite shaped body may be used in a variety of orthopaedic procedures involving bone repair and restoration. The present invention composite may be formed into a sleeve or cup. The bioactive antibacterial composite of the present invention may also be used in conjunction with orthopaedic appliances such as joints, rods, pins, suture fasteners, anchors, repair devices, rivets, staples, tacks, orthopaedic screws and interference screws. Such bioactive antibacterial composite shaped bodies can be used in conjunction with biocompatible gels, pastes, cements or fluids and surgical techniques that are known in the art. Thus, a shaped body comprised of the present invention composite material can be inserted into bone and the bioactivity and antibacterial properties of the material will give rise to osteogenesis and beneficial medical or surgical results.

Many of the embodiments disclosed herein are to fill bony voids and defects. It will be appreciated that applications for the embodiments of the present invention include, but are not limited to, filling interbody fusion devices/cages (ring cages, cylindrical cages), placement adjacent to cages (i.e., in front of cages), placement in the posterolateral gutters in posterolateral fusion (PLF) procedures, backfilling the iliac crest, acetabular reconstruction and revision hips and knees, large tumor voids, use in high tibial osteotomy, burr hole filling, and use in other cranial defects. The bone graft material strips may be suited for use in PLF by placement in the posterolateral gutters, and in onlay fusion grafting. Additional uses may include craniofacial and trauma procedures that require covering or wrapping of the injured/void site. The bone graft material cylinders may be suited to fill spinal cages and large bone voids, and for placement along the posterolateral gutters in the spine.

Figure 2A:
FIG. 2A illustrates one basic form of the bioactive antibacterial graft material in cylinder form.
Figure 2B:
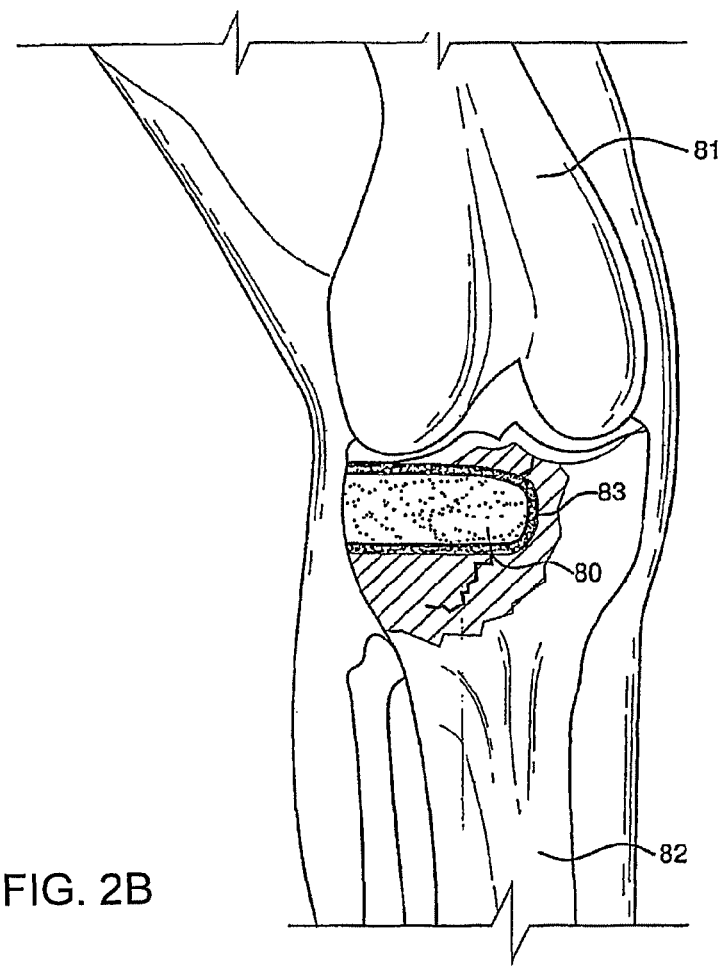
FIG. 2B depicts the graft material in cylindrical form 80 inserted into a bone void 83 below the femur 81 in the tibial plateau 82 within a human knee.
Figure 3:
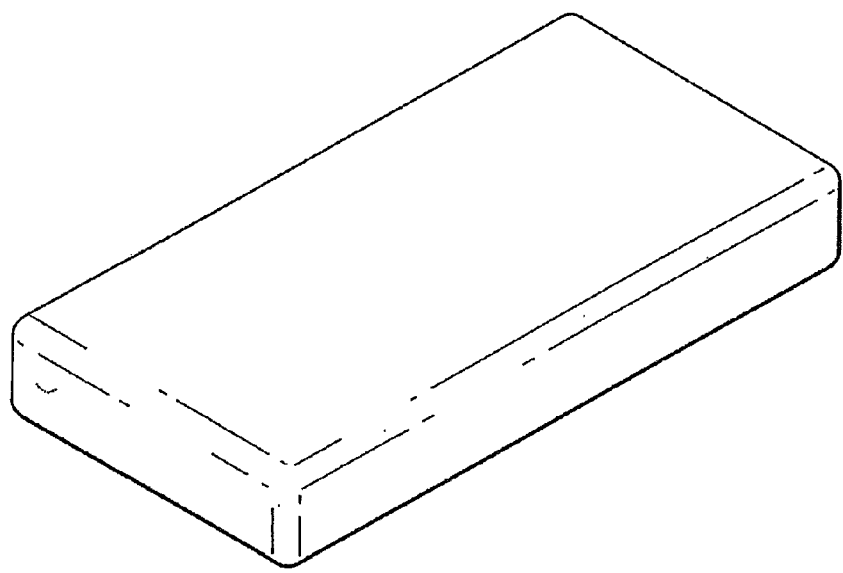
FIG. 3 illustrates another basic form of the present invention in strip form.

Due to the wide range of applications for the embodiments of the present invention, it should be understood that the present invention graft material could be made in a wide variety of shapes and sizes via standard molding techniques. For instance, blocks and cylinders of the present invention may find utility in bone void filling and filling of interbody fusion devices; wedge shaped devices of the present invention may find utility in high tibial osteotomies; and strips may find utility in cranial defect repairs. FIGS. 2A and 2B show the material of the present invention within a human tibia that is used as a block for bulk restoration or repair of bulk defects in bone or oncology defects.

Figure 4A:
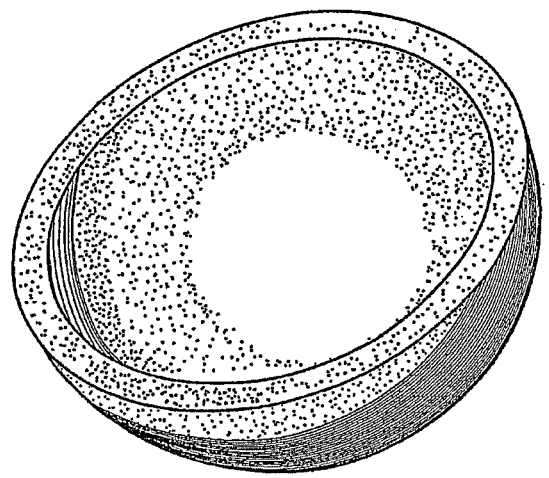
FIG. 4A illustrates one embodiment of the bioactive antibacterial graft material of the present invention in semi-spherical form used as a graft containment device.
Figure 4B:
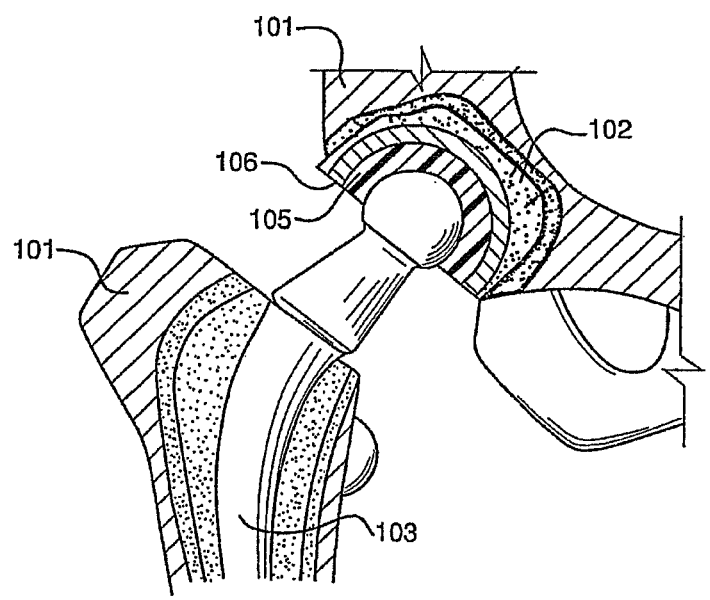
FIG. 4B depicts a semi-spherical form of the graft material 102 used to accommodate an artificial implant 103. The graft material 102 contains an acetabular cup 106, which holds a polyethylene cup 105, in this embodiment.
Figure 5A:
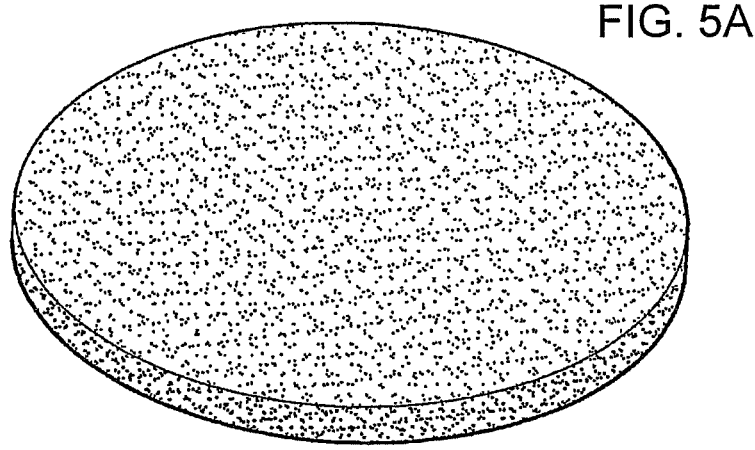
FIG. 5A illustrates the graft material of the present invention in disc form.
Figure 5B:
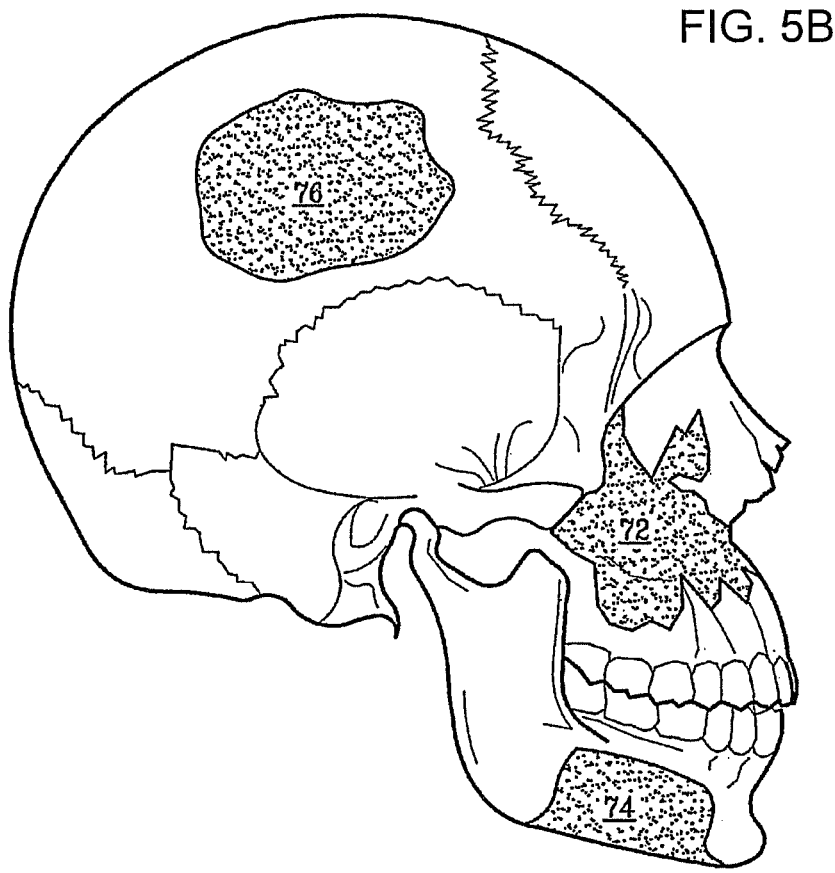
FIG. 5B illustrates another embodiment of the bioactive antibacterial graft material of the present invention used as a cranio-maxillofacial 76, zygomatic reconstruction 72, and mandibular implant 74.
Figure 6:
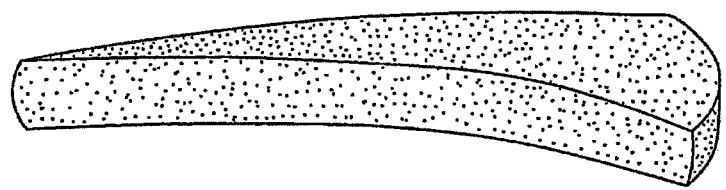
FIG. 6 illustrates one embodiment of a bioactive antibacterial graft material described shaped into a block/wedge form and used as a tibial plateau reconstruction that is screwed, bonded, cemented, pinned, anchored, or otherwise attached in place.

Of particular interest, may be the use of some of the graft materials as semi-spherical (FIG. 4A), semi-tubular (FIGS. 8A-8C) or disc-shaped (FIG. 5A) strips for graft containment devices. An embodiment of the semi-spherical form 102 in use is depicted in FIG. 4B.

It will be appreciated that these shapes are not intended to limit the scope of the invention as modifications to these shapes may occur to fulfill the needs of one skilled in the art. The benefits of the graft containment materials that, for instance, may be used in acetabular reconstruction made from the present invention are several-fold. The graft materials may act as both a barrier to prevent migration of other implants or graft materials and serves as an osteoconductive resorbable bone graft capable of promoting bone formation. The graft containment device may be relatively non-load-bearing, or partially load-bearing, or may be reinforced to be fully load-bearing as described below. Depending on the form, the graft materials have barrier properties because it maintains its structural integrity.

Figure 7A:
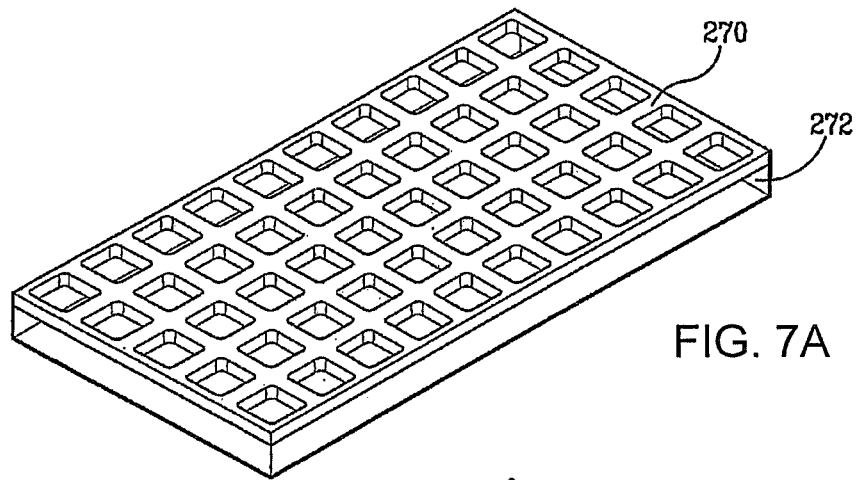
FIGS. 7A and 7B illustrate synthetic resorbable defect filling bone graft materials 272 for bone restoration having mesh 270 attached to one side.
Figure 7B:
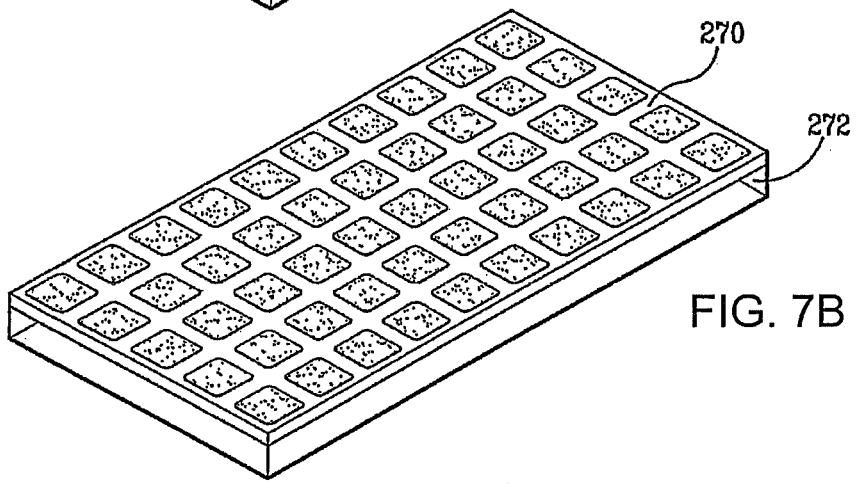
Figure 7C:
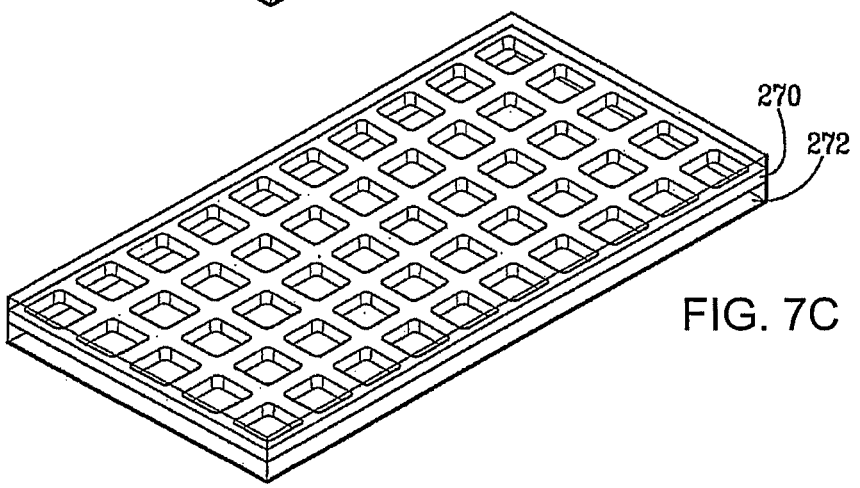
FIG. 7C depicts a synthetic resorbable defect filling bone graft material block in which the mesh 270 is sandwiched between the graft material 272.
Figure 8A:
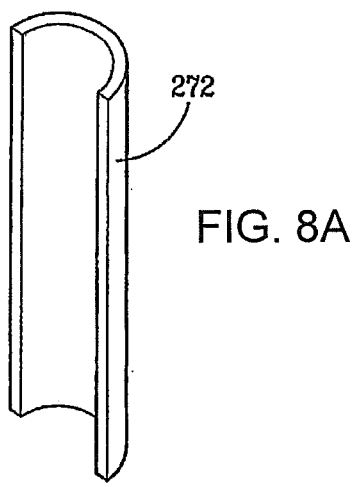
FIGS. 8A, 8B, and 8C illustrate an embodiment of the bioactive antibacterial graft material of the present invention in semi-tubular form used as a long bone reinforcement sleeve. As shown in the figures, the semi-tube may have a moon cross-section with a uniform thickness (FIG. 8A); or a crescent moon cross-section with a tapered radius that comes to a point (FIG. 8B) or a tapered radius that is rounded on the edges (FIG. 8C).
Figure 8B:
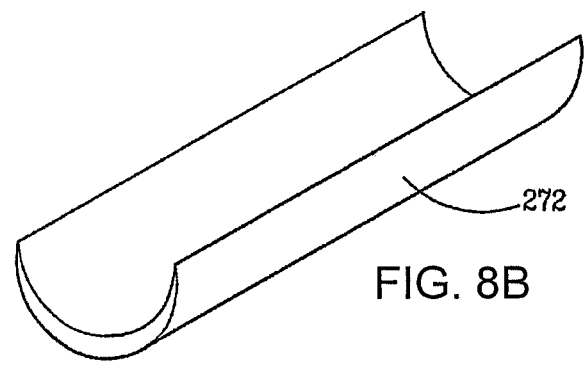
Figure 8C:
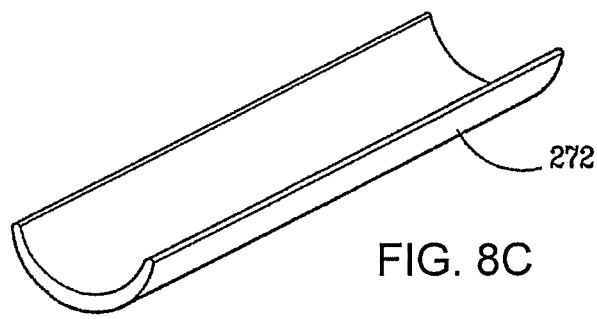

In applications requiring graft materials with load-bearing capabilities, the graft materials of the present invention may have meshes or plates affixed. The meshes or plates may be of metal, such as titanium or stainless steel, or of a polymer or composite polymer such as polyetheretherketone (PEEK), or nitinol. As depicted in FIGS. 7A and 7B, a metallic mesh 270 may be placed to one side of the bone graft material 272 to add strength and load-bearing properties to the implant. In FIG. 7A, the mesh plate 270 sits affixed to one surface of the graft material 272. In FIG. 7B, the mesh plate 270 penetrates one surface of the graft material 272 with one side of mesh exposed on top. In FIG. 7C, the mesh plate 270 is immersed more deeply than in FIG. 7B within the graft material 272. FIGS. 8A-8C depict another embodiment of the graft material 272 in semi-tubular form. A mesh may be affixed to a surface for further support in long bone reinforcement. Due to the unique properties of the present invention graft material, the mesh may be affixed in the body using sutures, staples, screws, cerclage wire or the like.

One skilled in the art may place the mesh in any location necessary for a selected procedure in a selected bodily void. For instance, a composite of mesh and graft material could be used in a craniomaxillofacial skull defect with the more pliable graft surface being placed in closer proximity to the brain and the more resilient mesh surface mating with the resilient cortical bone of the skull. In this manner, the mesh or plate may be affixed to one side of the graft material. Alternatively, the mesh or plate may be affixed to both sides of the graft material in sandwich fashion. Likewise, graft material could be affixed to both sides of the mesh or plate. In some embodiments, the mesh may be immersed within the graft material. The meshes may be flat or may be shaped to outline the graft material such as in a semi-spherical, semi-tubular, or custom form. These embodiments may be unique due to their integral relation between the graft material and the mesh. This is contrary to other products in the field in which the graft material is placed adjacent to the structural implant or, in the case of a cage, within the implant.

In accordance with the present invention, another embodiment provides a bone graft for long bone reinforcement comprising a biocompatible, resorbable semi-tubular shape, or sleeve, of β-tricalcium phosphate, collagen, and bimodal bioactive glass, the entire graft having interconnected macro-, meso-, and microporosity. A mesh may be affixed to the surface of the sleeve or may be immersed in the sleeve. The mesh may be made of titanium, stainless steel, nitinol, a composite polymer, or polyetheretherketone. The cross-section of the sleeve may be in the shape of a crescent shape moon (FIG. 8B).

In other embodiments, there is a graft for the restoration of bone in the form of a shaped body, the shaped body comprising β-tricalcium phosphate, collagen, and bimodal bioactive glass, the material of the graft having interconnected macro-, meso-, and microporosity; the body shape being selected to conform generally to a mammalian, anatomical bone structure. The shapes will vary depending on the area of the body being repaired. Some basic shapes may be a disk, semi-sphere, semi-tubular, or torus. In some embodiments, the shape will conform generally to the acetabulum.

Other graft materials of the present invention having load-bearing capabilities may be open framed, such that the bone graft material is embedded in the central opening of the frame. The frame may be made of a metal such as titanium or of a load-bearing resorbable composite such as PEEK or a composite of some form of poly-lactic acid (PLA). In the case of the latter, the acid from the PLA co-acts, or interacts with the calcium phosphate of the embedded bone graft material to provide an implant with superior resorption features.

The graft materials can also be imbibed with any bioabsorbable polymer or film-forming agent such as polycaprolactones (PCL), polyglycolic acid (PGA), poly-L-Lactic acid (PL-LA), polysulfones, polyolefins, polyvinyl alcohol (PVA), polyalkenoics, polyacrylic acids (PAA), polyesters and the like. The resultant graft material is strong, carveable, and compressible. The grafts of the present invention coated with agents such as the aforementioned may still absorb blood.

In another embodiment of the present invention, the graft materials may be used as an attachment or coating to any orthopaedic implant such as a metal hip stem, acetabular component, humeral or metatarsal implant, vertebral body replacement device, pedicle screw, general fixation screw, plate or the like. The coating may be formed by dipping or suspending the implant for a period of time in a substantially homogenous slurry of calcium phosphate, collagen, and bioactive glass and then processing via freeze-drying/lypholization and crosslinking techniques. As used in this context, substantially homogenous means that the ratio of elements within the slurry is the same throughout. Alternatively, a female mold may be made of the implant and the slurry may be poured into the mold and processed, as described above, to form the coating.

In yet another embodiment of the present invention, the graft material may be shredded or cut into small pieces. These smaller shredded pieces could then be used as filler or could be placed in a syringe body. In this fashion, fluids could be directly aspirated into or injected into the syringe body thereby forming a cohesive, shapeable bone graft mass "in situ" depending upon the application requirements. The shredded pieces find particular use as filler for irregular bone void defects. Further, unlike traditional bone graft substitutes they are highly compressible and therefore can be packed/impacted to insure maximum contact with adjacent bone for beneficial healing.

The bioactive composite of the present invention may also find particular utility in a variety of dental bone grafting procedures.

The collagen and bioactive glass may be combined with the calcium phosphate by blending to form a substantially homogenous mixture. As used in this context, substantially homogenous means that the ratio of components within the mixture is the same throughout. The calcium phosphate, collagen, and bioactive glass may also be combined to form a composite matrix in various shapes and sizes. In certain embodiments, the bioactive glass could be in the form of a coating on the collagen strands. In others, the bioactive glass could be in the form of a coating on a collagen and calcium phosphate homogenous mixture. Upon treatment using various preferred heating, freeze-drying, and crosslinking techniques, such mixtures of the present invention form graft materials that may be preferred. In one method, the three constituents (the inorganic component, collagen, and bioactive glass), are mixed while the pH of the homogenate is monitored. The bioactive component is sensitive to aqueous environments, so monitoring the pH of the homogenate ensures that the bioactive glass component in the mix is not altered via premature leaching of ions that are necessary for promoting osteoactivity and bioactivity and for maintaining antibacterial properties. The homogenate is then dispersed into defined molds, freeze-dried, and for some embodiments, crosslinked.

In another method, the collagen and the inorganic component are combined as described, and the bioactive glass is provided as a distinct component, to be incorporated into the bone graft material during preparation for use in the surgical site. Contemplated herein is a kit comprising a bone graft and bioactive glass. The bone graft provided in a kit may comprise collagen and calcium phosphate. In a kit, the bioactive glass may be provided in a unit dose, or two unit doses in which the two distinct glass particle sizes are separated, to be combined with the bone graft provided at the time of surgery. The bioactive glass may be provided in a single container or multiple containers. The components may be mixed together with fluid at the time of surgery to form a pliable, putty-like bioactive antibacterial bone graft substitute.

Certain aspects of the present invention provide for kits that contain sterile shaped implants within sterile packaging alongside appropriate instrumentation for inserting or implanting the shaped implant. For instance, the bone graft provided in a kit may be enclosed in a delivery apparatus, such as a syringe, or, the bone graft may be provided in addition to a syringe capable of holding and delivering the bone graft. Flowable bone graft materials (such as those described in U.S. Patent Application No. 2005/0288795, filed on Jun. 23, 2004, incorporated herein by reference in its entirety) are contemplated as being particularly suitable for such a kit. The bioactive glass may be within the delivery or holding apparatus along with the graft, or the bioactive glass may be provided in a second apparatus, such as a syringe. The bioactive-glass-containing apparatus may be adapted to connect to the bone graft apparatus such that homogenous mixing back and forth is permitted. Thus, ultimately, a composite apparatus capable of mixing the components into a substantially homogenous flexible, pliable bone graft containing calcium phosphate, collagen, and bioactive glass is provided.

The shaped bodies can be modified in a number of ways to increase or decrease their physical strength and other properties so as to lend those bodies to still further modes of employment. Overall, the present invention is extraordinarily broad in that shaped bodies may be formed easily and with enormous flexibility. Preformed shapes may be formed in accordance with the invention from which shapes may be cut or formed.

Throughout this disclosure, various aspects of the invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 10 to 40 should be considered to have specifically disclosed subranges such as from 10 to 30, from 10 to 20, from 20 to 40, from 15 to 35, from 13 to 26 etc., as well as individual numbers within that range, for example, 10, 20, 25.5, 30, 31.3, 35, and 40. This applies regardless of the breadth of the range.

EXAMPLES

Additional objects, advantages, and novel features of this invention will become apparent to those skilled in the art upon examination of the following examples of the invention. The examples are included to more clearly demonstrate the overall nature of the invention. The examples are exemplary, not restrictive, of the invention.

Example 1

Figure 9A:
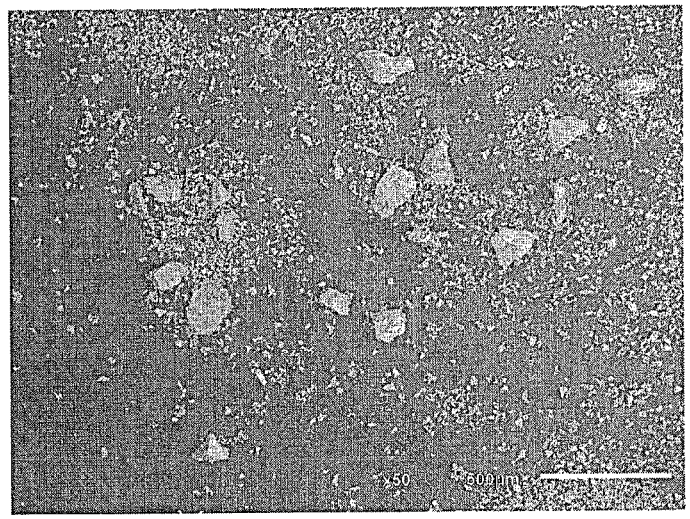
FIGS. 9A, 9B and 9C are scanning electron microscope (SEM) images of one embodiment of the present invention in morsel form showing the bimodal particle size range of the glass (<53 µm and 90 µm-150 µm).
Figure 9B:
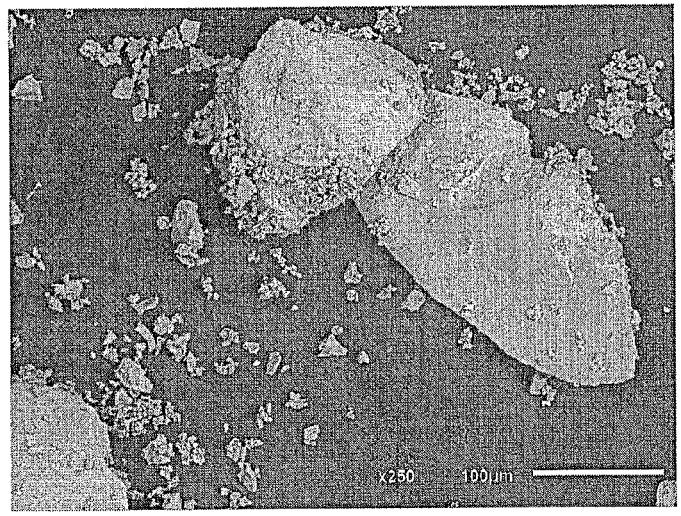
Figure 9C:
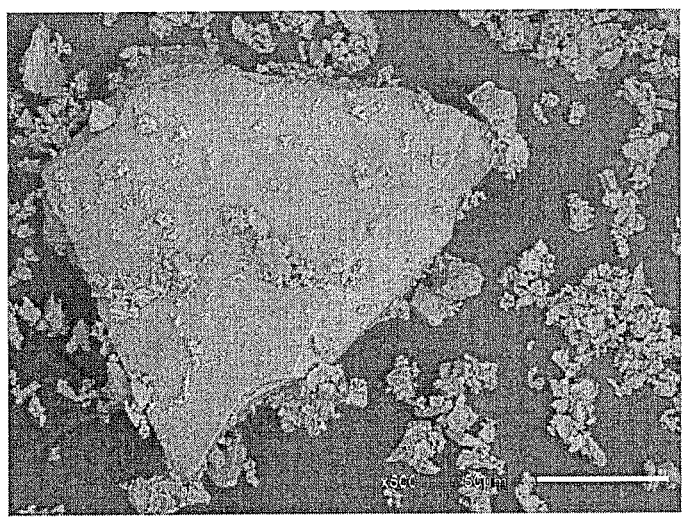
Figure 10:
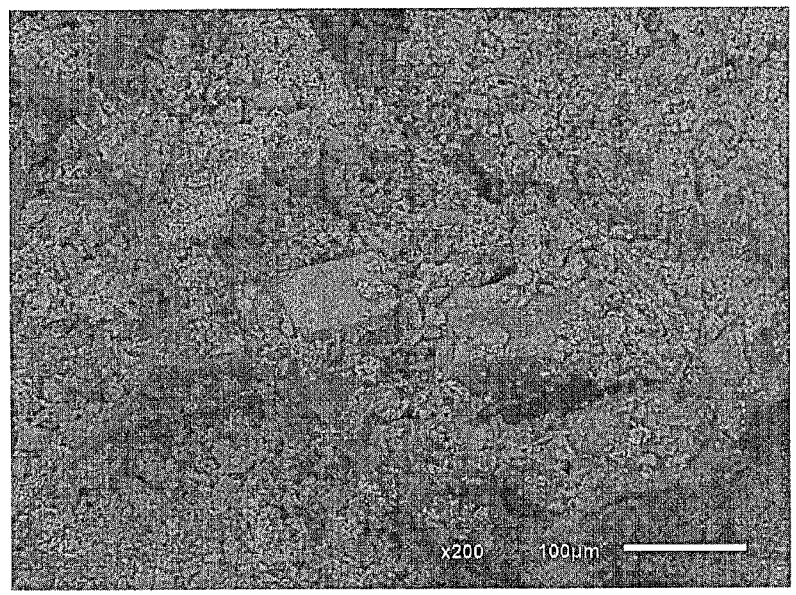
FIG. 10 is an SEM image (×200 magnification) of another embodiment of the present invention comprising beta-tricalcium phosphate and collagen in combination with the bimodal glass (i.e., Combeite glass-ceramic (<53 μm and 90 μm-150 μm)).

Scanning Electron Microscopy (SEM) Images of Several Embodiments of the Present Invention Scanning electron microscopy (SEM) was performed to qualitatively evaluate the bimodal nature of the bioactive glass of the present invention in morsel form and as part of a composite. FIGS. 9A, 9B and 9C are representative SEM images of the present invention showing bimodal Combeite glass-ceramic particles <53 µm in size and from about 90 µm-150 µm in size at three different magnifications—×50 magnification (FIG. 9A), ×250 magnification (FIG. 9B) and at ×500 magnification (FIG. 9C). FIG. 10 is a representative SEM image of another embodiment of the present invention in composite form in which the bimodal Combeite glass-ceramic comprises about 20% by weight of the composite, the beta-tricalcium phosphate comprises about 65% by weight of the composite and collagen comprises about 15% by weight of the composite (×200 magnification).

Example 2

Laser Scattering Particle Size Distribution Analyzer Evaluation

Figure 11:
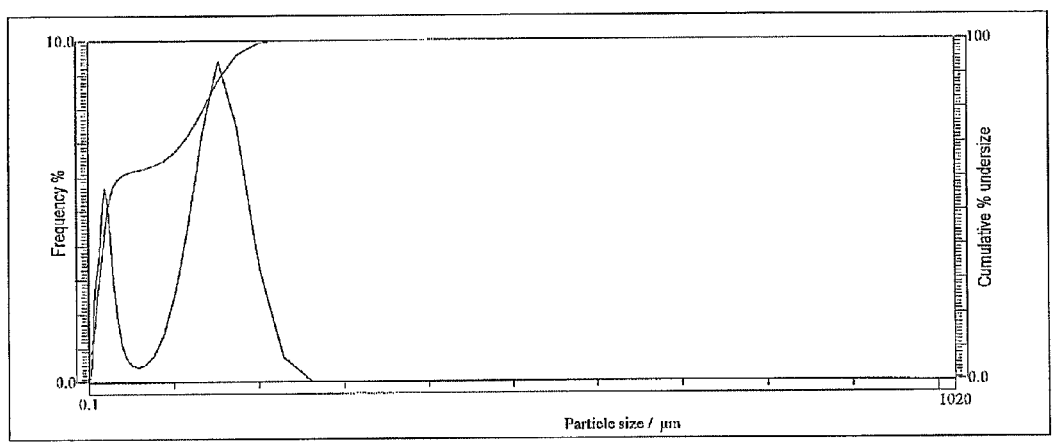
FIG. 11 shows and exemplary particle size distribution graph of bimodal glass according to the present invention embodiment shown in FIGS. 9A, 9B and 9C.
Figure 12:
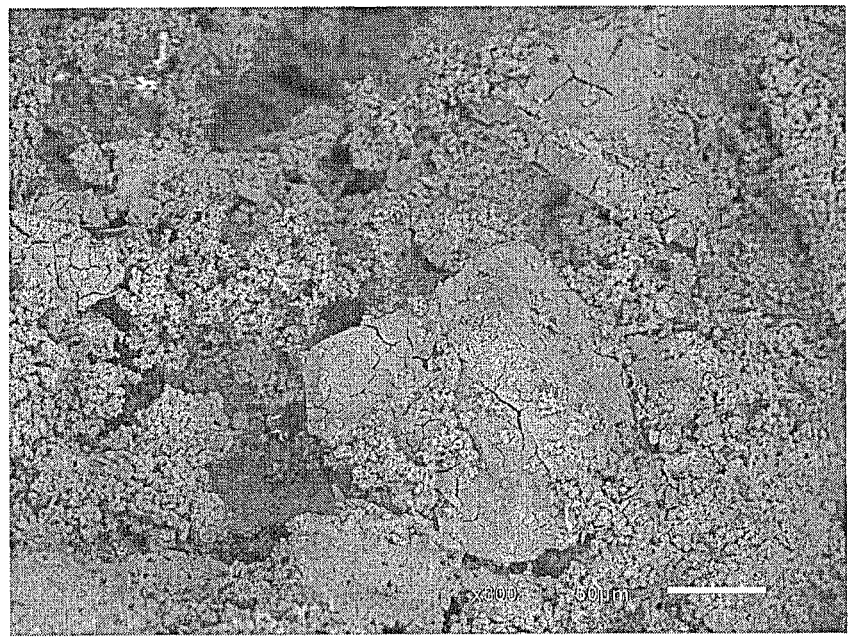
FIG. 12 depicts an SEM image (×300 magnification) of the embodiment shown in FIG. 10 representing the bioactive nature of the material after submersion in simulated body fluid (SBF) for 1 day.
Figure 13:
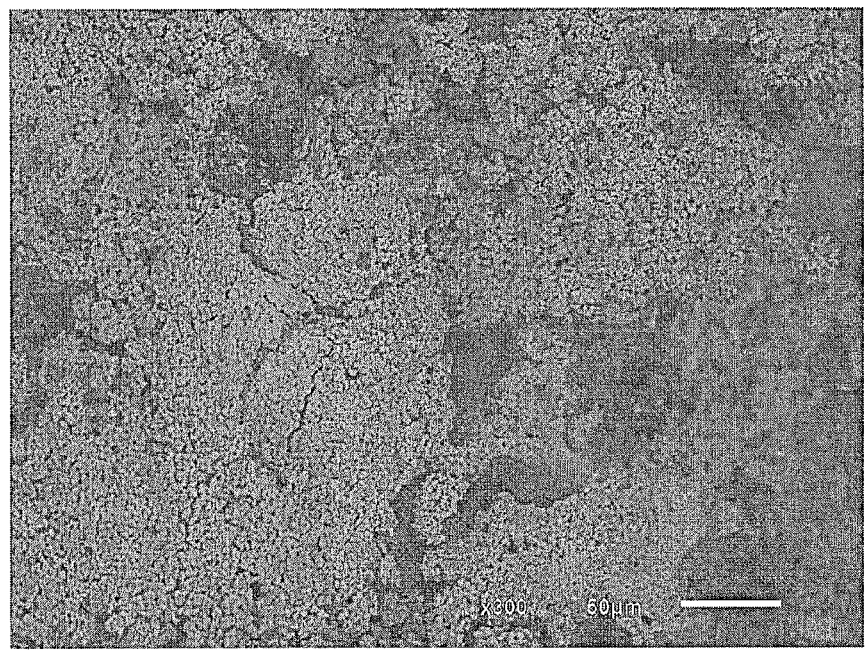
FIG. 13 depicts an SEM image (×300 magnification) of the embodiment shown in FIG. 10 representing the bioactive nature of the material after submersion in simulated body fluid (SBF) for 3 days.
Figure 14:
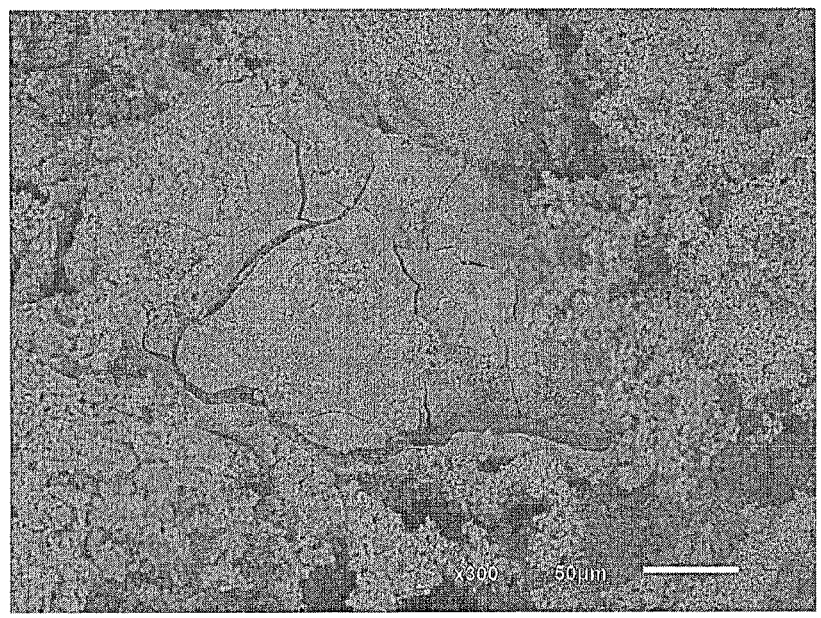
FIG. 14 depicts an SEM image (×300 magnification) of the embodiment shown in FIG. 10 representing the bioactive nature of the material after submersion in simulated body fluid (SBF) for 7 days.
Figure 15:
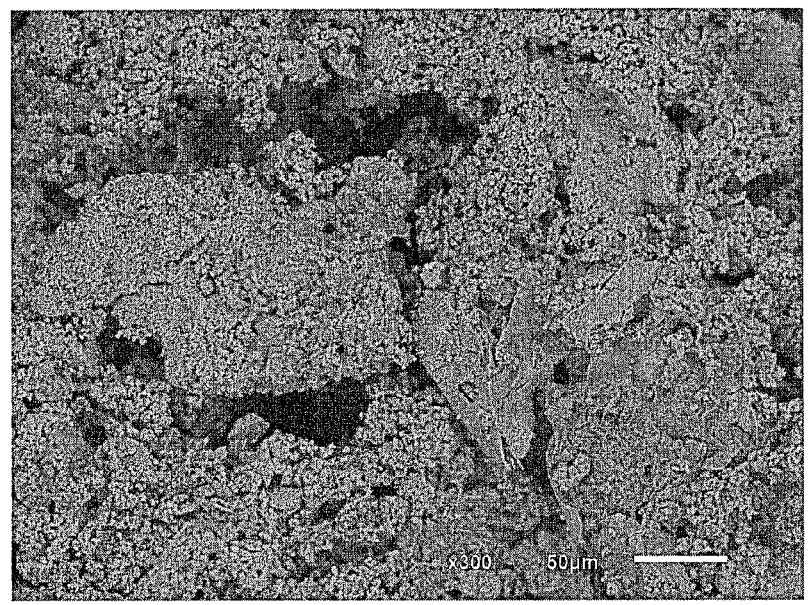
FIG. 15 depicts an SEM image (×300 magnification) of the embodiment shown in FIG. 10 representing the bioactive nature of the material after submersion in simulated body fluid (SBF) for 14 days.

Particle size distribution of the bimodal glass of the present invention was performed using a laser scattering particle size distribution analyzer (Horiba LA-910). This analytical technique provides information on the D10 (particle size for which 10% of the particle size distribution is below this value), D50 (particle size for which 50% of the particle size distribution is below this value) and D90 (particle size for which 90% of the particle size distribution is below this value). Bimodal Combeite glass-ceramic particles (<53 µm in size and from about 90 µm-150 µm in size) were analyzed in triplicate. Approximately 50% of the particles, by weight, were below 53 microns in size while approximately 50% of the particles, by weight, were between 90-150 microns in size. An exemplary particle size distribution graph of the bimodal glass is shown in FIG. 11. The D10 of this particle size distribution was between about 2 and about 6 microns, the D50 was between about 20 and about 25 microns, and the D90 was between about 150 and about 160 microns.

Example 3

In-Vitro Bioactivity

In vitro bioactivity studies were performed with the test materials of the present invention using the method of Kokubo, *How useful is SBF in predicting in vivo bone bioactivity*, Biomaterials (2006) 27:2907-2915. Samples were made by combining a strip of calcium phosphate and collagen (Vitoss® (VT) Foam Pack Bone Graft Substitute (Orthovita, Inc., Malvern, Pa.)) with bimodal Combeite bioactive glass-ceramic particles. Fifty percent (50%) by weight of the glass particles were about <53 µm in size and 50% by weight of the glass particles were between about 90-150 µm in size. An amount of saline approximately equal to the volume of strip material was added to the strip along with the glass-ceramic particles, and all materials were kneaded together for approximately 2 minutes to form a putty-like ("pack") composite material. The final ratio of calcium phosphate:collagen:bimodal glass was approximately 65:15:20. The samples were suspended in simulated body fluid at 37° C. for 1, 3, 7 and 14 days (FIGS. 12, 13, 14 and 15, respectively). After immersion in SBF, the formation of a significant amount of calcium phosphate was observed on the composite material even as early as 1 day.

Example 4

Wettability and Compression Resistance

Pliable "pack" samples were made by combining a strip of calcium phosphate and collagen with bimodal Combeite bioactive glass-ceramic particles as described above in Example 3. Fifty percent (50%) by weight of the glass particles were about <53 µm and 50% by weight of the glass particles were between about 90-150 µm in size. Two concentrations of the bimodal Combeite were tested—100 mg of Combeite per mL of bone graft (equal to a calcium phosphate:collagen:bimodal glass ratio of approximately 65:15:20) and 200 mg of Combeite per mL of bone graft (equal to a calcium phosphate:collagen:bimodal glass ratio of approximately 54:14:32). The pack materials were inserted into a syringe and a mechanical testing device was used to apply a constant pressure on the plunger of the syringe, thereby compressing the material being tested, until a pressure of approximately 30 lbf was reached. The weights of the materials before and after compression were recorded and used to calculate the fluid retention capability of the material (Table 1).

TABLE 1

| Bimodal glass concentration (mg/mL) | Dry weight (g) | Hydrated weight (g) | Mass increase | Hydrated weight after compression (g) | Fluid retention |
|---|---|---|---|---|---|
| 100 | 2.8154 | 5.8524 | 207.9% | 5.8056 | 99.2% |
| 200 | 3.3274 | 7.2804 | 218.8% | 7.2128 | 99.1% |

Example 5

Radiopacity

Figure 16:
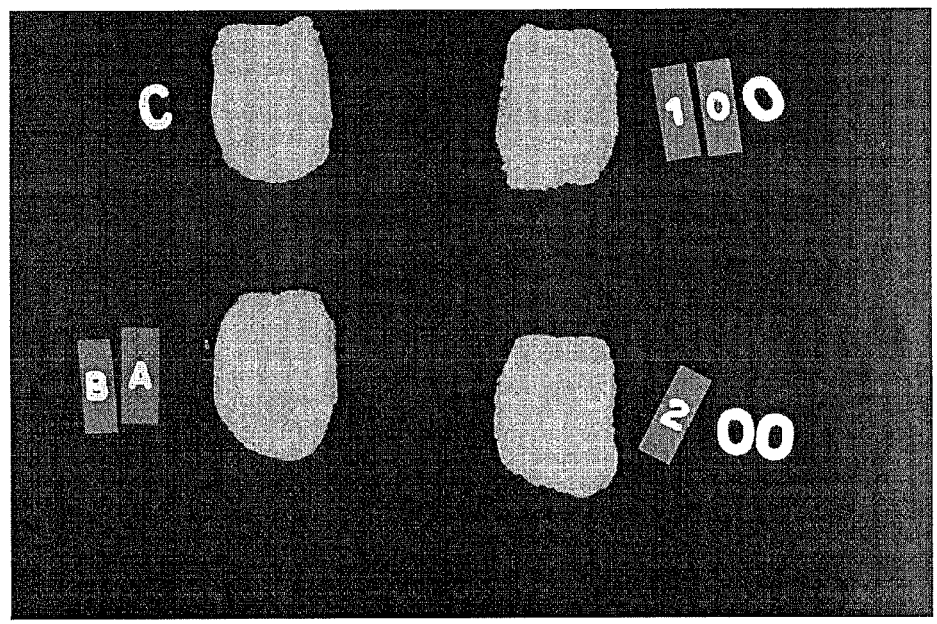
FIG. 16 is a faxitron image of various embodiments of the present invention (in putty-like or "pack" form) comprising beta-tricalcium phosphate and collagen admixed with the bimodal glass showing the radiopacity of each in comparison to materials that do not contain the bimodal glass particle distribution.

A faxitron high-resolution x-ray was taken of the present invention materials, prepared as described above in Examples 3 and 4. The radiopacity of the present invention embodiments was similar to that of controls that did not contain bioactive glass in a bimodal particle size range (FIG. 16). Note: "C"—VT Foam Pack Bone Graft Substitute (Orthovita, Inc., Malvern, Pa.) control; "BA"-Vitoss™ BA Bioactive Bone Graft Substitute (Orthovita, Inc., Malvern, Pa.) control; "100"—present invention material with 100 mg of bimodal Combeite per mL of bone graft in which fifty percent (50%) by weight of the glass particles were about <53 µm in size and 50% by weight of the glass particles were between about 90-150 µm in size; and "200"—present invention material with 200 mg of bimodal Combeite per mL of bone graft in which fifty percent (50%) by weight of the glass particles were about <53 µm in size and 50% by weight of the glass particles were between about 90-150 µm in size. The exposure was 60 kV for 60 seconds.

Example 6

Performance Testing of Bioactive Antibacterial Material

The antibacterial effects of a bimodal particle size distribution of Combeite bioactive glass-ceramic were evaluated. Antibacterial efficacy was investigated against *Staphylococcus aureus*, *Escherichia coli*, and *Pseudomonas aeruginosa* for the glass alone as well as the glass combined with VT Foam Pack Bone Graft Substitute (prepared as described above in Examples 3 and 4 with the addition of a 50 mg/mL group, equivalent to a calcium phosphate:collagen:bimodal glass ratio of approximately 70:20:10).

For testing of the bioactive (BA) glass particles, bimodal glass consisting of 50%<53 µm particles and 50% 90-150 µm particles by weight was added to tryptic soy broth (TSB) at a concentration of 100 mg/mL. The mixture was then inoculated with 0.5×10⁶ colony forming units (CFU)/mL of *S. aureus*, *E. coli*, or *P. aeruginosa*. This concentration represents the physiologic level of bacteria necessary to cause wound infection (Robson, Surg Clin North Am, 1997). After 1, 7, or 14 days, an aliquot was taken, serially diluted, and plated to count colonies. For testing of bimodal bioactive glass with VT Foam Pack Bone Graft Substitute (VT Foam Pack), glass particles were combined with the VT Foam Pack to equivalent concentrations of 50, 100, and 200 mg/mL of bone graft material and kneaded in a sterile manner as per the manufacturer's instructions. The mixture was then inoculated with $0.5\times10^6$ CFU/mL and placed in a sealed container. After an incubation period, the mixture was added to broth and shaken vigorously to release any bacteria from the bone graft composite. An aliquot was taken, serially diluted, and plated for counting. Control samples with no added glass were tested in the same manner. Test methods are based on the United States Pharmacopeia <51> Standard.

Table 2 demonstrates the log reductions of the smaller <53 μm particles, which demonstrate efficacy against 3 strains of bacteria at a concentration of 50 mg/mL. Table 3 illustrates the log reductions of the larger 90-150 μm particle size. Negative log reductions indicate that this particle size alone was not effective at reducing levels of bacteria present, even at a higher 100 mg/mL concentration.

Table 4 demonstrates the antibacterial efficacy of a bimodal distribution of particles against 3 strains of bacteria. A greater than 4 log reduction was seen at 1 day, and this antibacterial efficacy was maintained over the course of 14 days indicating that all microorganisms were killed within the first 24 hours of exposure. A 4 log reduction demonstrates 99.99% efficacy.

TABLE 2

<53 μm bioactive glass Log CFU/mL Reductions at 24 hours

| Organism | 50 mg/mL |
|---|---|
| S. aureus | 2.2 |
| P. aeruginosa | >4.6 |
| E. coli | >4.8 |

TABLE 3

90-150 μm bioactive glass Log CFU/mL Reductions at 24 hours

| Organism | 50 mg/mL | 100 mg/mL |
|---|---|---|
| S. aureus | −4.0 | −4.1 |
| P. aeruginosa | −4.2 | −4.1 |
| E. coli | −3.9 | −3.5 |

TABLE 4

100 mg/mL bimodal bioactive glass Log CFU/mL Reductions

| Organism | 1 day | 7 day | 14 day |
|---|---|---|---|
| S. aureus | >4.7 | >4.7 | >4.7 |
| P. aeruginosa | >4.6 | >4.6 | >4.6 |
| E. coli | >4.8 | >4.8 | >4.8 |

Figure 17:
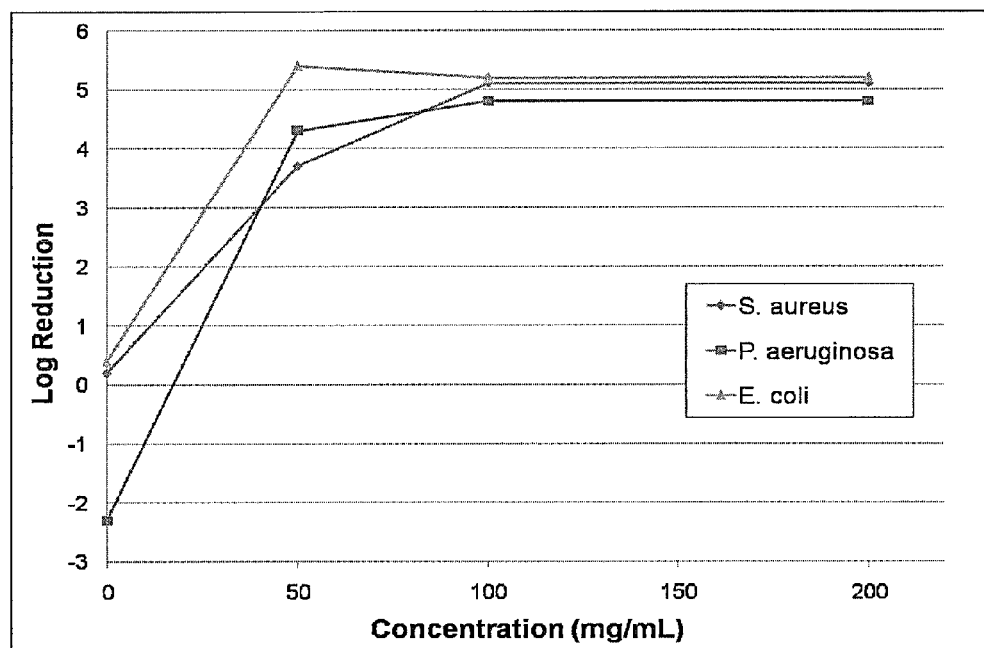
FIG. 17 is a graphical depiction of the log reduction achieved at 1 day for increasing concentrations of bimodal glass incorporated into a bone graft substitute of collagen and calcium phosphate.

FIG. 17 and Table 5 illustrate the log reduction achieved at 1 day for increasing concentrations of bimodal glass admixed with the VT Foam Pack. Increasing amounts of glass yielded higher log reduction of bacteria until 100 mg/mL was reached. At 100 and 200 mg/mL, BA glass combined with VT Foam Pack yielded an approximate 5 log reduction, or 99.999% efficacy. Without the bioactive glass component there was no antibacterial efficacy observed.

TABLE 5

Vitoss PACK with bimodal glass Log CFU/ml Reductions at 24 hours

| Organism | 0 mg/mL | 50 mg/mL | 100 mg/mL | 200 mg/mL |
|---|---|---|---|---|
| S. aureus | 0.2 | 3.7 | 5.1 | >5.1 |
| P. aeruginosa | −2.3 | 4.3 | >4.8 | >4.8 |
| E. coli | 0.4 | 5.4 | >5.2 | >5.2 |

Table 6 demonstrates the antibacterial efficacy of VT Foam Pack with 100 mg/mL bimodal glass over the course of 28 days. There is a greater than 4 log reduction seen at 1 day, and this antibacterial efficacy was maintained over the course of 28 days indicating that all microorganisms were killed within the first 24 hours of exposure to the antibacterial bone graft.

TABLE 6

100 mg/mL bimodal bioactive glass with Vitoss Pack Log CFU/mL Reductions

| Organism | 1 day | 7 day | 14 day | 28 day |
|---|---|---|---|---|
| S. aureus | 5.1 | >5.1 | >5.1 | >5.1 |
| P. aeruginosa | >4.8 | >4.8 | >5.1 | >5.1 |
| E. coli | >5.2 | >5.2 | >5.3 | >5.3 |

*Inoculations for all antibacterial efficacy testing were performed at approximately 5.7 log CFU/mL This testing demonstrates that a bimodal distribution of BA glass combined with a bone graft substitute of collagen and calcium phosphate possesses antibacterial properties. It is believed that a primary mechanism of action of BA glass is the release of ions into the surrounding medium. Several investigators have found that these ions cause changes in osmotic pressure (Stoor P. Acta Odontol Scand. 1996; 56 (3):161-165), an increase in pH (Allan I. Biomaterials. 2001; 22:1683-1687), and release of calcium ions causing membrane perturbations in the bacteria (Munukka E. J Mater Sci: Mater Med. 2008; 19:27-32), all factors that play a role in creating inhibitory conditions for bacteria. The small particle sizes in the bimodal distribution have a dissolution rate necessary for immediate ion release, accounting for the demonstrated antibacterial efficacy. Conversely, the larger and slower reacting particles of the bimodal distribution provide benefits for bone healing (Havener M B. Presented at ORS. 2009). These dual advantages provide clinical benefits by reducing the incidence of surgical site infections as well as increasing the rate of bone healing.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A bioactive antibacterial composite comprising a biocompatible polymer, a porous calcium phosphate and a bioactive glass, wherein the bioactive glass consists of:
   (a) particles having a particle size of less than about 53 microns (μm) and
   (b) particles having a particle size range from about 90 microns (μm) to about 150 microns (μm),
   wherein the biocompatible polymer is present in an amount from about 10% to about 20% by weight of the composite, the calcium phosphate is present in an amount from about 50% to about 75% by weight of the composite and the bioactive glass is present in an amount from about 10% to about 35% by weight of the composite, and
   wherein the bioactive antibacterial composite has antibacterial efficacy of greater than about 3.7 log reduction at 1 day when tested based on USP <51> standard at a bioactive glass concentration of between about 50 to about 200 mg/mL.

2. The bioactive antibacterial composite of claim 1, wherein the biocompatible polymer is collagen.

3. The bioactive antibacterial composite of claim 1, wherein the calcium phosphate is beta-tricalcium phosphate.

4. The bioactive composite of claim 1, wherein the bioactive glass is 45S5 or Combeite.

5. The bioactive antibacterial composite of claim 1, wherein the composite has a total porosity of at least 30% and interconnected macro-, meso- and microporosity.

6. The bioactive antibacterial composite of claim 1, wherein the biocompatible polymer is collagen and the calcium phosphate is beta-tricalcium phosphate.

7. A bioactive antibacterial composite comprising a biocompatible polymer, a porous calcium phosphate and a bioactive glass, wherein about 50% by weight of the bioactive glass comprises particles with a particle size of less than about 53 μm and about 50% by weight of the bioactive glass comprises particles having a particle size range from about 90 μm to about 150 μm, wherein the bioactive antibacterial composite has antibacterial efficacy of greater than about 3.7 log reduction at 1 day when tested based on USP <51> standard at a bioactive glass concentration of between about 50 to about 200 mg/mL.

8. A method for repairing a defect in bone and preventing surgical site infection comprising the step of administering the bioactive antibacterial composite of claim 1 or 7 to the bone.

9. The method of claim 8, wherein the defect is a defect in the spine.

10. The method of claim 8, wherein the defect is a defect in the vertebral body.

11. A method for repairing a damaged bone or tooth comprising placing the bioactive antibacterial composite of claim 1 or 7 in the bone or jaw.

12. The bioactive antibacterial composite of claim 7, wherein the biocompatible polymer is collagen.

13. The bioactive antibacterial composite of claim 7, wherein the calcium phosphate is beta-tricalcium phosphate.

14. The bioactive composite of claim 12, wherein the bioactive glass is 45S5 or Combeite.

15. The bioactive antibacterial composite of claim 7, wherein the composite has a total porosity of at least 30% and interconnected macro-, meso- and microporosity.

16. The bioactive antibacterial composite of claim 7, wherein the biocompatible polymer is collagen and the calcium phosphate is beta-tricalcium phosphate.

* * * * *